(12) United States Patent
Vander Meer et al.

(10) Patent No.: US 8,865,152 B2
(45) Date of Patent: Oct. 21, 2014

(54) METHODS AND COMPOSITIONS FOR ATTRACTING OR REPELLING COCKROACHES

(75) Inventors: Robert K Vander Meer, Gainesville, FL (US); Richard J Brenner, Washington, DC (US); Domonic A Cataldo, Kennewick, WA (US); Peter Van Voris, Kennewick, WA (US); Edward S Lipinsky, Worthington, OH (US)

(73) Assignees: The United States of America, as represented by the Secretary of Agriculture, Washington, DC (US); Bioguard Research and Development, Inc., Kennewick, WA (US)

( * ) Notice: Subject to any disclaimer, the term of this patent is extended or adjusted under 35 U.S.C. 154(b) by 0 days.

(21) Appl. No.: 13/529,569

(22) Filed: Jun. 21, 2012

(65) Prior Publication Data

US 2012/0315242 A1    Dec. 13, 2012

Related U.S. Application Data

(62) Division of application No. 12/221,344, filed on Aug. 1, 2008, now Pat. No. 8,273,340.

(51) Int. Cl.
*A01N 25/00* (2006.01)
*A01N 37/02* (2006.01)
*A01P 19/00* (2006.01)
*A01N 37/06* (2006.01)

(52) U.S. Cl.
CPC ............... *A01N 37/02* (2013.01); *A01N 37/06* (2013.01)
USPC ........................................................... 424/84

(58) Field of Classification Search
None
See application file for complete search history.

(56) References Cited

U.S. PATENT DOCUMENTS

| 3,523,101 | A | * | 8/1970 | Reuter | ............................. 528/79 |
| 4,156,067 | A | * | 5/1979 | Gould | ......................... 424/78.06 |
| 2004/0231231 | A1 | * | 11/2004 | Cataldo et al. | ............... 43/132.1 |

OTHER PUBLICATIONS

Sugawara et al., "Attraction of the German Cockroach to Cyclohexyl Alkanoates and n-Alkyl Cyclohexaneacetates" J. Insect Physiol., 1975, vol. 21, pp. 957-964.*
Leblanc, Jean L., "Nonlinear viscoelastic characterization of molten thermoplastic vulcanizates (TPV) through large amplitude harmonic experiments" Rheol Acta (2007), vol. 46: pp. 1013-1027.*
Nojima, S. et al., "Identification of the Sex Pheromone of the German Cockroach, Blattella germanica", Science 307, 2005, pp. 1104-1106.

* cited by examiner

*Primary Examiner* — Abigail Fisher
*Assistant Examiner* — Daniel L Branson
(74) *Attorney, Agent, or Firm* — John D. Fado; Byron Stover (57) ABSTRACT

A method for attracting cockroaches to an object or area, involving treating said object or area with a cockroach attracting composition containing a cockroach attractant effective amount of at least one compound selected from the group consisting of methyl, ethyl, propyl, or butyl esters of $C_{3-7}$ saturated or unsaturated carboxylic acids and mixtures thereof, and optionally a carrier material or carrier. A method for repelling cockroaches from ah object or area, involving treating said object or area with a cockroach repelling composition containing a cockroach repelling effective amount of at least one compound selected from methyl, ethyl, propyl, or butyl esters of $C_{3-7}$ saturated or unsaturated carboxylic acids or mixtures thereof, and optionally a carrier material or carrier.

14 Claims, 8 Drawing Sheets

METHODS AND COMPOSITIONS FOR ATTRACTING OR REPELLING COCKROACHES

This is a divisional of application Ser. No. 12/221,344, filed 1 Aug. 2008, which is herein incorporated-by reference in its entirety.

BACKGROUND OF THE INVENTION

The present invention relates to a method for attracting cockroaches to an object or area, involving treating the object or area with a cockroach attracting composition containing a cockroach attracting effective amount of at least one compound selected from methyl, ethyl, propyl, or butyl esters of $C_{3-7}$ saturated or unsaturated carboxylic acids or mixtures thereof, and optionally a carrier material or carrier. The present invention also relates to a method for repelling cockroaches from an object or area, involving treating said object or area with a cockroach repelling composition containing a cockroach repelling effective amount of at least one compound selected from methyl, ethyl, propyl, or butyl esters of $C_{3-7}$ saturated or unsaturated carboxylic acids or mixtures thereof, and optionally a carrier material or carrier.

Cockroaches are perhaps the most common and troublesome household pest in the United States (ranked second worst urban pest insect, just behind pest ants) and most of the world. Cockroaches are not only a nuisance in the home but also can spread disease organisms from garbage, sewers, and other sources to human food that can then cause dysentery, food poisoning, and diarrhea. In addition, some of the most common allergens in homes are from the cockroach and its feces, which cause allergic rhinitis and asthma.

Currently, there are two approaches to controlling cockroaches. One approach uses liquid sprays containing pesticide that are sprayed where cockroaches are likely to travel or seek harborage. This approach relies on the cockroach coming in contact with the pesticide. The other approach is the use of bait products, e.g. "roach motels". The two methods may be used by themselves or in combination, and the applicator may be a pest control operator (PCO) or homeowner. It is estimated that over US$500M worth of "roach motels" are sold every year worldwide, and it is estimated that the combined "spray" and "roach motel" market exceeds US$1.3 billion annually.

An attractant is a chemical that causes an organism (e.g., cockroach) to make oriented movement towards its source. Currently, there are no commercially available cockroach attractants used in cockroach control. The term attractant is often erroneously used in reference to phagostimulants (food) that must be found randomly, e.g., by cockroaches, or must be placed in an area known to be frequently visited by cockroaches. Most of the published "attractant" formulations have involved the use of cockroach feces which is not commercially practical and may add to allergic rhinitis and asthma problems already associated with cockroach feces. U.S. Pat. No. 5,665,370 describes methods to collect and to sterilize the active ingredients in cockroach feces and to separate them into sterilized attractants and aggregation pheromones. This is an improvement but not commercially satisfactory. U.S. Pat. No. 5,505,591 describes numerous synthetic pyrans and also mentions three sex pheromones: periplanone B, periplanone A, and periplanone J. U.S. Pat. No. 5,126,128 describes Periplanone-B analogues with pheromone activity. Simpler chemicals are found in U.S. Pat. No. 5,384,120 where propyl cyclohexyl acetate was utilized as an aggregation pheromone for the German cockroach and the combination of isobornyl acetate and santalol alone or in conjunction with propyl cyclohexyl acetate were utilized for attracting cockroaches. These acetates, pyrans, and pheromone analogues represent the state of the art. However, they are still inadequate.

Thus there is a need to develop cockroach attractants that are based on simple chemicals and processes and that provide safe and effective cockroach attraction as well as delivery systems that can provide an effective dose over a reasonable period of time.

SUMMARY OF THE INVENTION

In accordance with the present invention there is provided a method for attracting cockroaches to an object or area, involving treating said object or area with a cockroach attracting composition containing a cockroach attracting effective amount of at least one compound selected from the group consisting of methyl, ethyl, propyl, or butyl esters of $C_{3-7}$ saturated or unsaturated carboxylic acids and mixtures thereof, and optionally a carrier material or carrier.

Also in accordance with the present invention is a method for repelling cockroaches from an object or area, involving treating said object or area with a cockroach repelling composition containing a cockroach repelling effective amount of at least one compound selected from methyl, ethyl, propyl, or butyl esters of $C_{3-7}$ saturated or unsaturated carboxylic acids or mixtures thereof, and optionally a carrier material or carrier.

DETAILED DESCRIPTION OF THE INVENTION

The present invention concerns a composition which attracts cockroaches, and contains, methyl, ethyl, propyl, or butyl esters of $C_{3-7}$ saturated or unsaturated carboxylic acids or mixtures thereof, and optionally a carrier or carrier material known in the art. The carboxylic acids range from three to seven carbons and may contain an $\alpha$, $\beta$-unsaturation (i.e., the double bond is alpha, beta to the carboxylic add carbon). Such compounds include ethyl propanoate, ethyl pentanoate, ethyl hexanoate, propyl propanoate, butyl hexanoate, butyl heptanoate, methyl tiglate, ethyl caproate, and mixtures thereof.

The present invention also concerns a method for attracting cockroaches to an object (e.g., insect trap) or area (e.g., field, orchard), involving treating (or exposing) the object or area with a composition containing a cockroach attracting effective amount of methyl, ethyl, or propyl esters of $C_{3-7}$ saturated or unsaturated carboxylic acids or mixtures thereof, and optionally a carrier or carrier material.

The amount of attractant used will be at least an effective amount. The term "effective amount," as used herein, means the minimum amount of attractant needed to attract the cockroaches to a treated area or object when compared to the same area or object which is untreated. Effective concentrations of the attractant in the compositions may vary between about 0.00001% to about 99.99% (preferably about 0.00001% to about 50%, more preferably about 0.00001% to about 10%, more preferably about 0.00001% to about 1%, more preferably about 0.00001% to about 0.1%, more preferably about 0.00001% to about 0.01%). Of course, the precise amount needed will vary in accordance with the particular attractant composition used; the type of area or object to be treated; the number of days of attractiveness needed; and the environment in which the area or object is located. The precise amount of attractant can easily be determined by one skilled in the art given the teaching of this application. For example, one skilled in the art could follow the procedures utilized below; the attractant would attract more than 50% (or 65%) of the cockroaches and would be statistically significant in comparison to a control. The attractant composition may or may not contain a control agent for cockroaches, such as a biological control agent or an insecticide known in the art to kill cockroaches. Other compounds may be added to the attractant composition provided they do not substantially interfere with the intended activity of the attractant composition; whether or not a compound interferes with attractant activity can be determined, for example, by the procedure utilized below. Such other compounds may be present generally from about 0.0025% to about 20% in the composition.

The attractants, in combination with a suitable toxicant or toxic bait, could direct the target cockroaches to toxic baits, rather than have the discovery a random event. In this way toxic baits will be quicker acting, could be placed in locations away from human activity, or may be used as cockroach infestation monitors that could trigger treatment. The attractants used in combination with contact toxicants or other non-toxic mechanisms to trap cockroaches may be able to effectively reduce cockroach populations below reaction levels.

While the compounds defined above were attractive to cockroaches, they were by nature volatile. It is envisioned that commercially useful compositions will combine an effective amount of attractant with a carrier. The carrier or carrier material may be, for example, agronomically or physiologically or pharmaceutically acceptable carriers or carrier material. The carrier may be liquid or solid and in either case release effective amounts of attractant over time periods greater than could be achieved with the attractant alone. The carrier may be a cockroach food material (phagostimulant) already used in cockroach bait stations or may be inert. Inert carriers may, for example, consist of diatomaceous earth, alumina, clays, cornstarch, or cellulose. Slow release solid carriers could consist of polymers, microencapsulation, or other methods well developed in the controlled release industry. Two basic low cost sustained-release delivery (SRD) systems were investigated: (A) the first involves absorbing the active to a substrate (reservoir) that is then secondarily coated/encapsulated to limit diffusion of the volatile to air and control the release rate. Absorbents may consist of various types of charcoal or amorphous silica. A secondary coating (methyl cellulose, polyvinyl acetate, cellulose acetate, ethylene adipate polyester, polyacrylates, carboxymethyl cellulose, hydroxypropyl cellulose, poly(ethylene oxide), crosslinked starch, or crosslinked cellulose) is then applied to the absorbed attractant. (B) The second delivery system is to microcapsulate the attractant, which can then be absorbed into the large pore spaces of a carrier reservoir, such as amorphous silica. Secondary encapsulation may be required to further reduce the rates of attractant loss and to increase longevity of the bioactive SRD system.

The present invention also concerns a method for repelling cockroaches from an object or area, involving treating said object or area with a cockroach repelling composition containing a cockroach repelling effective amount of at least one compound selected from methyl, ethyl, propyl, or butyl esters of $C_{3-7}$ saturated or unsaturated carboxylic acids or mixtures thereof, and optionally a carrier material or carrier. Such compounds include propyl butanoate, butyl propanoate, butyl butanoate, hexyl butanoate, and mixtures thereof.

The amount of repellant used will be at least an effective amount. The term "effective amount," as used herein, means the minimum amount of repellant needed to repel the cockroaches from a treated area or object when compared to the same area or object, which is untreated. Effective concentrations of the repellant in the compositions may vary between about 0.00001% to about 99.99% (preferably about 0.00001% to about 50%, more preferably about 0.00001% to about 10%, more preferably about 0.00001% to about 1%, more preferably about 0.00001% to about 0.1%, more preferably about 0.00001% to about 0.01%). Of course, the precise amount needed will vary in accordance with the particular repellant composition used; the type of area or object to be treated; the number of days of repellant activity needed; and the environment in which the area or object is located. The precise amount of repellant can easily be determined by one skilled in the art given the teaching of this application. For example, one skilled in the art could follow the procedures utilized below; the repellant would repel more than 50% (or 65%) of the cockroaches and would be statistically significant in comparison to a control. The repellant composition may or may not contain a control agent for cockroaches, such as a biological control agent or an insecticide known in the art to kill cockroaches. Other compounds may be added to the repellant composition provided they do not substantially interfere with the intended activity of the repellant composition; whether or not a compound interferes with repellant activity can be determined, for example, by the procedure utilized below. Such other compounds may be present generally from about 0.0025% to about 20% in the composition.

The cockroaches include, for example, *Blattella germanica, Periplaneta; americana, Blatta orientalis,* and *Supella supellectilium.*

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described.

The following examples are intended only to further illustrate the invention and are not intended to limit the scope of the invention as defined by the claims.

EXAMPLES

The German cockroach (*Blattela germanica*) is one of the most difficult cockroach species to control in homes and was used to illustrate the invention. The discovery of cockroach attractants was made possible through the development of a Y-Tube olfactometer that gave quick and reliable results. The system is capable of determining if a test compound or extract is an attractant, neutral, or repellent. Since the cockroaches never contact the test sample, their response is strictly to the molecules in the air stream.

Olfactometer Bioassay: The Y-tube bioassay apparatus was similar to that described by Vander Meer et al (J. Chem. Ecol., 14: 825-838 (1988)). Compressed air (breathing-air quality) was passed into the two choice arms at 0.2 l/min for a total flow of 0.4 l/min. Flow rates were adjusted and controlled by two flow meters (Omega Engineering, Inc.). All tubing carrying the air was either copper or Teflon. Prior to evaluating treatment samples, a positive standard was put through the bioassay procedure. The standard was initially an attractive food material (grape flavoring concentrate used at 0.33%) and later 0.5% (w/v) methyl tiglate, one of the compounds of the present invention, in white, light mineral oil (Aldrich Chemical Co.). Treatment evaluations were not started unless the positive standard showed significant cockroach attraction. Test samples (10.0 µl) and the solvent blank (mineral oil, 10.0 µl) were applied to filter paper strips (0.3×1.0 cm, Whatman No. 1) and then each was placed into one of the two choice arms. Male cockroaches (*Blattela germanica*) were prepared for their introduction into the olfactometer by placing them in a Teflon tube (3 cm×0.8 cm) that had one end blocked with a piece of copper mesh screen. The open end of tube was closed with a lightly attached piece of tape. The cockroaches were introduced individually by removing the tape and quickly inserting the Teflon tube into the entrance arm of the olfactometer. The screen mesh did not block the airflow and roaches generally moved upstream to the choice arms. The initial choice of the cockroach was recorded. The cockroach was removed and the process was repeated 10 times with the same test and blank samples. The 10 choices usually required less than 5 minutes to complete. After each set of 10 cockroaches had made their choice, the olfactometer was rinsed with acetone, dried, and reassembled for the next test. Each sample was retested with the same cockroaches but with the sample and control in reverse positions. The sum of the results from the two tests represented one replicate. This procedure minimized bias inherent in the apparatus. A null hypothesis of equal numbers of cockroaches in each arm was tested with chi-square analysis. Results where 65% or more of the roaches choose the sample side were significantly attractive, whereas 35% or less cockroaches going to the sample side represented significant repellent activity. Results in-between were neutral.

Figure 1:
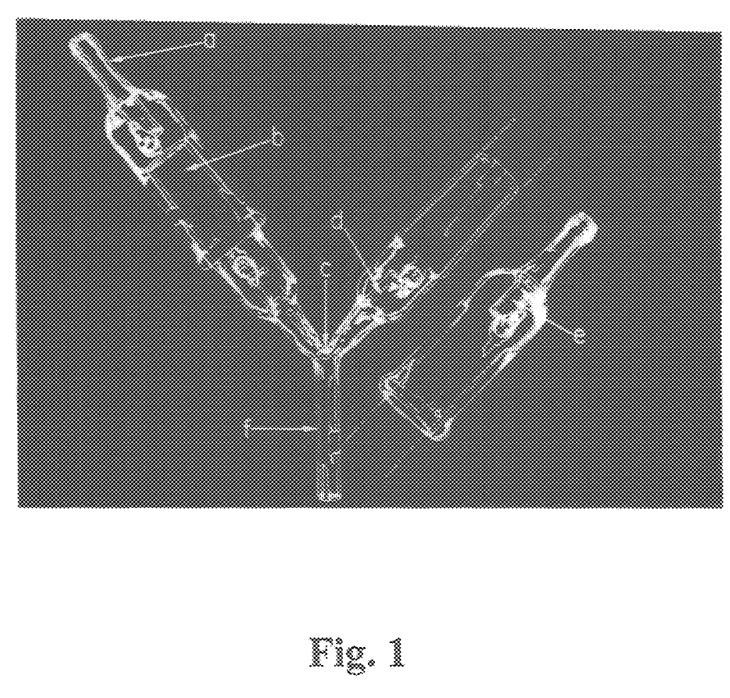
FIG. 1 is a photograph of the Y-tube olfactometer used in the evaluation of compounds as cockroach attractants: a=airflow into the olfactometer; b=sample or control locations; c=air baffle; d & e=ring seals which trap roaches in b; f=roach entrance arm.

Results: The results of the olfactometer bioassay for a series of methyl, ethyl, propyl, and butyl esters and one hexyl ester are shown in Table 1. Results are given as a percent response to a 0.5% w/v solution of the test compound in mineral oil. Results with an * after them were significantly attractive; compounds with ** after them were significantly repellent (mean of 3 replicates). The diameter of the Y part of the olfactometer provided a close fit for the cockroach, thus keeping it in the center of the walkway. The cockroaches readily walked up the entrance arm of the olfactometer. When they arrived at the Y juncture each antenna was usually sampling the airflow from a different choice arm of the olfactometer (see FIG. 1). Six compounds were shown to significantly attract cockroaches (percent response ≥65%). No methyl esters of saturated straight chain carboxylic acids were active in the bioassay. However, there were active ethyl, propyl and butyl esters. Three of the six active compounds were ethyl esters. Regarding the carboxylic acid moiety, there appears to be no pattern, as three, five, six and seven carbon chain lengths showed significant activity. Available homologues on either side of the active esters were inactive. Interestingly, four esters showed significant repellant activity, three of which were esters of butanoic acid (Table 1).

Figure 2:
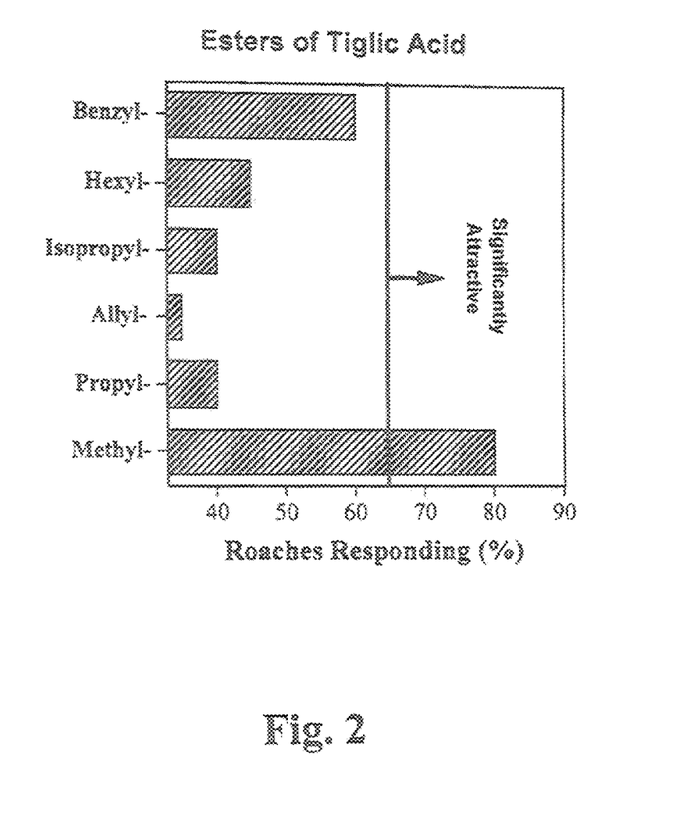
FIG. 2 shows olfactometer results for esters of tiglic acid. Results above 65% were significantly attractive and results below 35% were significantly repellent (mean of 3 replicates).

The methyl ester of tiglic acid (trans-2-methyl-2-butenoic acid (methyl tiglate)) showed excellent attractant activity (80.0%, see FIG. 2). Ester homologues of methyl tiglate were also evaluated. None of the five homologues tested had significant activity at the concentration used (0.5% w/v).

Figure 7:
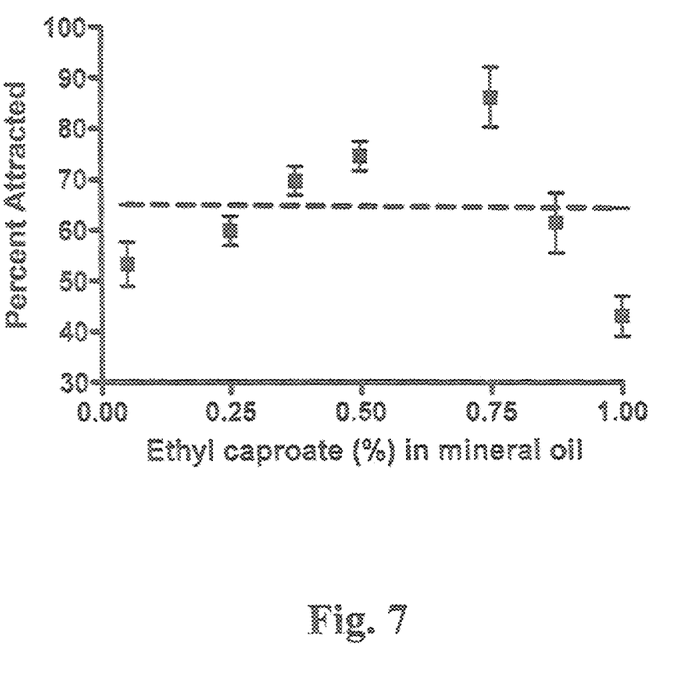
FIG. 7 shows the response of German cockroaches to the indicated concentration of ethyl caproate (ethyl hexanoate) dissolved in mineral oil. A mean response of 65% or greater represents significant attraction. The dashed line is a reference line at 65%. A response of 35% or below represents significant repellency. Significant attraction occurs between 0.25 and 0.85% (N=3).
Figure 8:
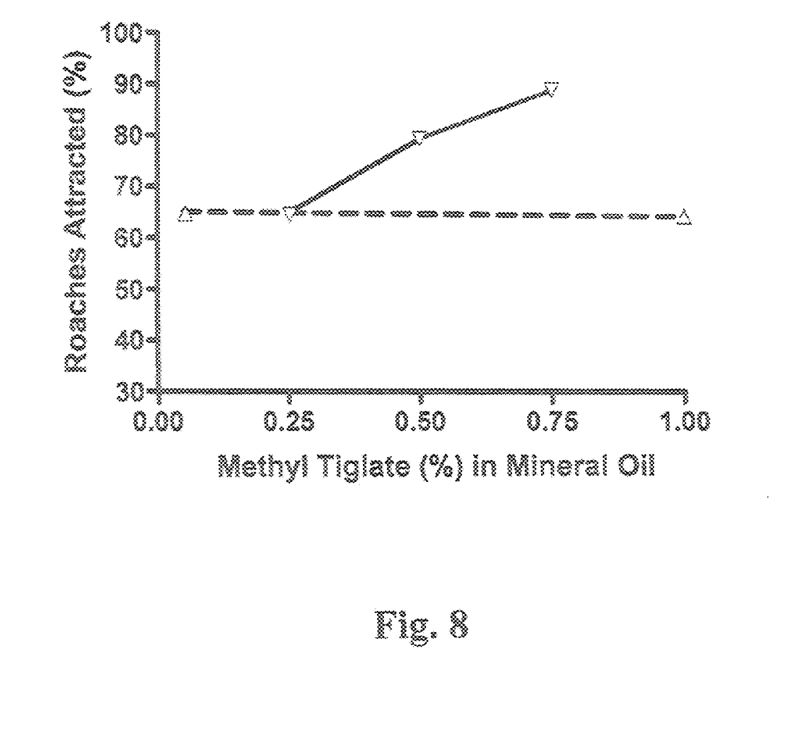
FIG. 8 shows the response of German cockroaches to the indicated concentration of methyl tiglate dissolved in mineral oil (N=1). A mean response of 65% or greater represents significant attraction. The dashed line is a reference line at 65%. A response of 35% or below represents significant repellency.

Ethyl caproate was used to evaluate the effect of concentration on cockroach attraction using the described olfactometer. Concentrations ranging from 0.0 to 1.0% w/v in mineral oil were evaluated. The results are shown in FIG. 7. Significant activity was found at concentrations between 0.25 and 0.9%. Another example is shown in FIG. 8 where methyl tiglate was evaluated at three concentrations (0.25 to 0.75). All concentrations attracted 65% or more of the responding cockroaches and were therefore attractive. It is important to demonstrate a range of active concentrations because it shows what kind of flexibility can be incorporated into the release rates of the formulated cockroach attractants.

Controlled Release Formulations: Four esters found to be significant cockroach attractants were selected for evaluation in controlled release formulations developed by BioGuard, Inc. Six controlled release formulations from BioGuard, Inc. were evaluated in the olfactometer. The attractants were methyl tiglate, butyl hexanoate, propyl propanoate, and butyl heptanoate. The attractants were absorbed to either coconut shell charcoal pellets or potassium substituted crystalline zeolite pellets, and then coated with water soluble methylcellulose. The powdered methyl cellulose was dissolved in 80° C. water until saturation, cooled to approx 25° C., the pellets immersed into the solution for a 30 sec, and removed and rapidly air dried with 30° C. pre-dried air. The end products were pellets (charcoal=2 mm×4 mm dia.; molecular sieve=4 mm×1.5 mm dia.). To prevent the possible confounding effects from the potentially high concentration of attractant accumulated in the vial holding the pellets, we placed the pellets needed for evaluation in a fume hood for one hour prior to olfactometer testing. A single pellet was used in place of the filter paper described above. The control side was left blank.

All four formulations (methyl tiglate, butyl hexanoate, propyl propanoate, and butyl heptanoate) using charcoal as the absorbent were significantly active in the olfactometer after one hour in the fume hood (Table 2). However, the two molecular sieve formulations were no different than the control (Table 2). Three of the active formulations shown in Table 2 were allowed to age for longer time periods in the fume hood to examine the longevity of their activity (Table 3). Methyl tiglate and butyl hexanoate maintained attract activity between 24 and 48 hours of aging, but butyl heptanoate lost attractant activity between 1 and 24 hours. It should be noted that the samples were aged in a fume hood with high air throughput, thus the longevity may be greater under more static conditions as might be expected in real usage situations.

Controlled or Sustained Release Systems for Cockroach Attractants: Three cockroach attractants identified above (propyl propanoate, butyl hexanoate, and methyl tiglate) were selected for further formulation in controlled release formulations. The attractants are active at the ppb/ppm level in air, and a system was needed to contain the active compounds while in storage (shelf-life) and also release effectively for at least 30 days when activated. Initial efforts to develop a sustained release system yielded release durations of hours to a few days, and were inadequate (Table 3). Common adsorbents and microporous materials failed to achieve either adequate air concentration or longevity. These included various plant and animal charcoals, crystalline zeolites, bentonite and montmorillinite clays, microporous polyethylene polymers, and mineral- and silicone-based oils (data not shown). Without being bound by theory, the problem was related to their vapor pressures which resulted in rapid volatilization to air, and/or their chemical reactivity.

Attempts were made to directly incorporate the active compounds into a variety of casting thermoset products, including polydimethylsiloxsiane-, hexamethyldisilazane-, methhyltrimethoxysilane-, methyltriacetoxysilane-based silicones, MDI (methylene diphenyl diisocyanate)-based urethanes, polystyrene. These failed to provide significant increases in release longevity. During these studies it was noted that the active compounds were acting as plasticizers with a number of thermoset urethane, styrene, and synthetic rubber materials, resulting in chemical incorporation into the polymerized polymers, and drastically reducing the amount and release rate of active components.

To alleviate the reactivity with the carrier polymers, we attempted to load active compounds into a series of thermoplastic polymers including urethanes and synthetic rubbers, based on the behavior of the active compounds as plasticizers. While injection molding failed to provide a viable system due to thermal losses and chemical pyrolysis, it was noted that there was a residual release that was better than other systems previously evaluated. Propyl propanoate; methyl hexanoate, and methyl tiglate were loaded into a series of thermoplastic granulated feed materials, including 4-(1,1,3,3-tetramethylbutyl) with ethylene-5-ethylidenebicyclo[2.2.1]hept-2-ene-propene thermoplastic synthetic rubber (Santoprene™ 203-40). Santoprene™ is a thermoplastic elastomer (TPE that is a mixture of in-situ cross linking of EPDM rubber and polypropylene compounds). Because of the longer life of Santoprene™ in both extreme hot and cold environments, it is often preferred over the use of rubber. Pellethane™ 2102-55D is a polyester polycaprolactone polyurethane. Methyl hexanoate and methyl tiglate were sorbed using heat and pressure (60° C., 40 psi, 30 min) into the Santoprene® and were effective in bioassays for cockroach attraction. Dow Pellethane™ worked less well, and neither of these systems worked well for propyl propanoate. Loading rates of active compounds into the Santoprene®, using slightly elevated temperature (60° C.) and 40 psi pressure, were 8-12% by wt for the two compounds.

A different delivery system was developed for propyl propanoate. To get around the reactivity problem, we developed a system using Devcon Flexane® 80 (a thermoset polymer consisting of polypropylene glycol and methylene bis(4-cyclohexylisocyanate), cured with diethyltoluenediamine). This thermoset polymer system required that the active compounds be preloaded into carrier particles (must remain friable prior to addition to polymer, not overloaded), and then incorporated into the thermoset system. The carrier that was most effective was the Nanocor Nanomer® I.3.0E (5 µm montmorillinite, octadecylammonium ion-substituted nanoclay), which can be loaded up to 50% by wt with active compounds. Nanoclay/active loading rates into the polymer were at 2 gm nanoclay/active (1 gm active) per 20.5 gm polymer. Release rates can be controlled by increasing or decreasing the cross linking by adjusting the ratio of catalyst to monomer. The preferred formulation for propyl propanoate and butyl hexanoate, consisted of 90 parts propylene glycol, 10 parts methylene bis(4-cyclohexylisocyanate) and cured with 38 parts of diethyltoluenediamine. For methyl tilgate 20 parts curing agent is preferred.

Figure 4:
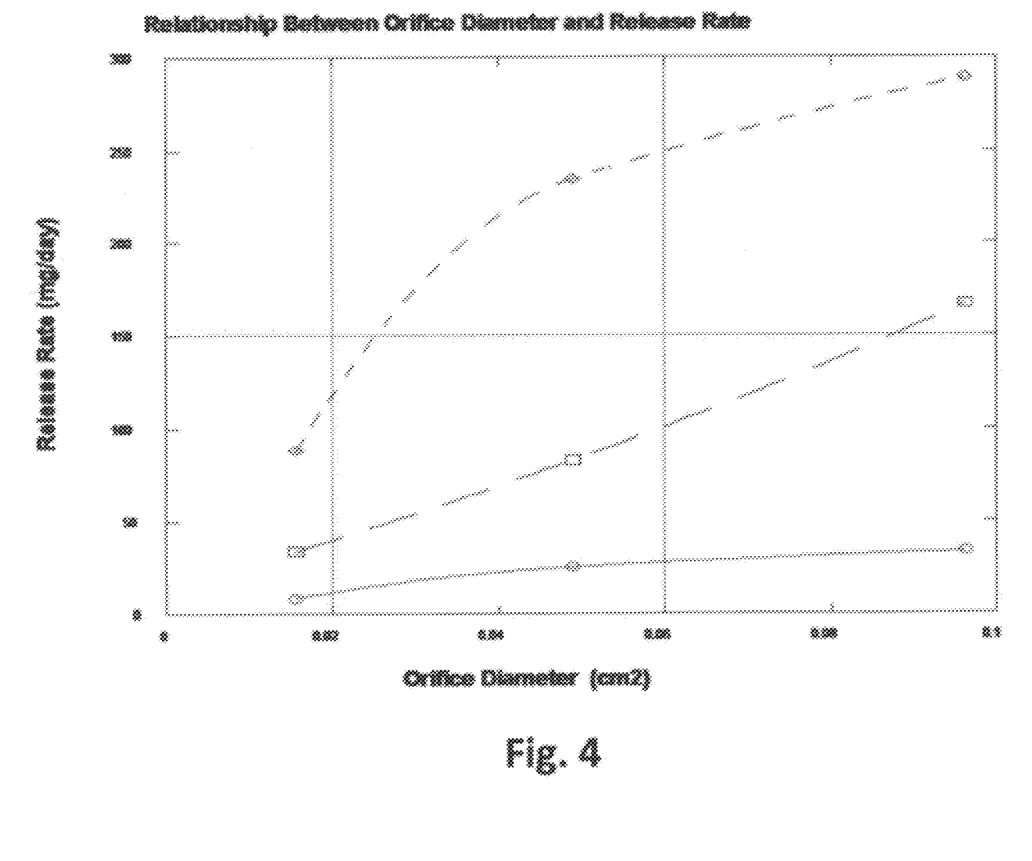
FIG. 4 shows relative release rates through pores based on orifice diameter and compound vapor pressure; propyl propionate (upper curve), methyl tiglate (middle), and butyl hexanoate (lower).
Figure 5:
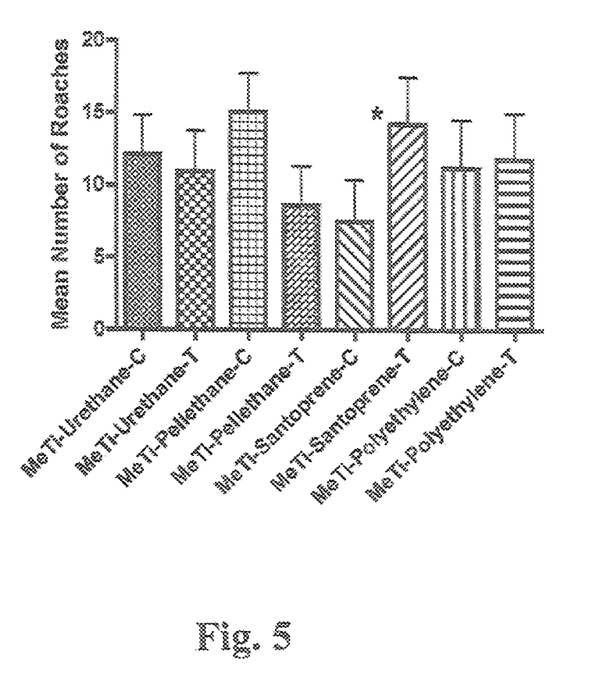
FIG. 5 shows bioassay results for methyl tiglate formulated with four different polymers (T) and their corresponding controls (C). Data is presented as the mean and standard error. *=Control and Treatment for a given formulation were significantly different.
Figure 6:
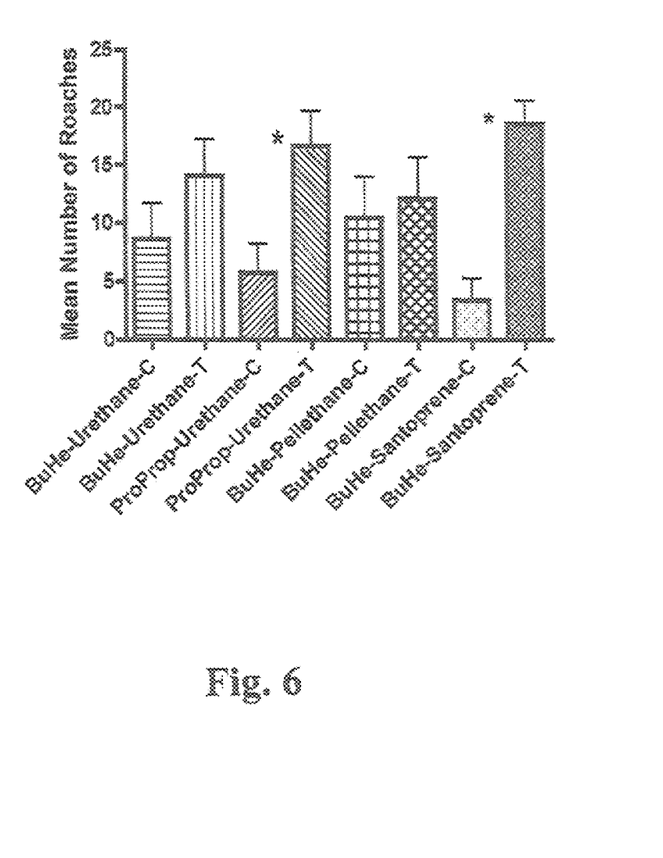
FIG. 6 shows bioassay results for propyl propanoate (Pro-Prop) and butyl hexanoate (BuHe) formulated with three different polymers (T) and their corresponding controls (C). Data is presented as the mean and standard error, *=Control and Treatment for a given formulation were significantly different.

While volatility losses of the active compounds due to vapor pressure can be dramatically reduced with these polymer/carrier systems, we still needed the ability to store and release at the bio-effective levels for specific cockroach control situations. Several secondary release rate control systems were developed. The first was a sachet that can contain the above polymer releasing system. This sachet can be either polyvinylidine chloride (PvdC) barrier film (e.g., Saranex™) enclosed in a thermally sealed metalized polyethylene container to eliminate release of active compounds, or a metalized polyethylene sachet with a removable seal that covers a vapor diffusion controlling orifice which when removed begins the release process from the internal polymer/carrier, or metalized polyethylene sachet which contains a small vial with a vapor controlling orifice. In the case of the Saranex™ sachet, the actual porosity of the Saranex™ control release is based on type of PVdC and thickness of the film. In the case of the metalized polyethylene sachet and internal polymer/carrier, a specific orifice size controlled the rate of diffusion of the active from the device, as shown in FIG. 4. An additional means of containing and reducing the release of the liquid active compounds and providing a solid support for use in the above delivery system involved sorbing the active compounds into an inert absorbent such as Membrana GmbH's expanded microporous polyolefin-Accurel® MP100 which are granular or pelletized polyethylenes that have 10-50 µm air pockets throughout and can contain up to 90% of their volume in active compounds. MP100 was easily loaded with 80% by wt active ingredient due to its porosity. Again, this material simply held the active, but did not provide sufficient diffusion reduction for adequate longevity of a releasing system. Thus, placement into the metalized polyethylene sachet with its diffusion regulating orifice was required.

Figure 3:
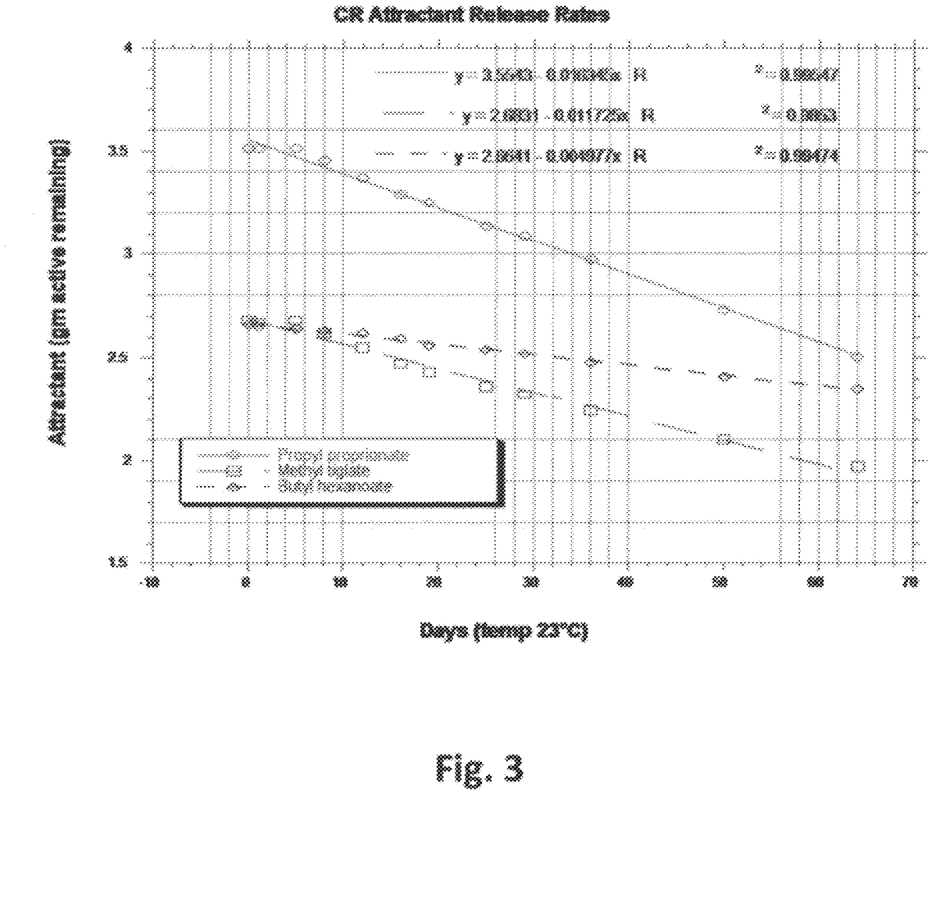
FIG. 3 shows release rates for bioactives sorbed into MP100 and released from a metalized polyethylene sachet containing a 0.5 mm orifice.

FIG. 3 shows the release rate profiles for three active compounds. Active compounds (1 gm active in Accurel® MP100) were sealed within the metalized polyethylene sachet, and a 0.5 mm hole placed into the film, and sealed until use with a metalized tape. Release rates for propyl propanoate, methyl tiglate, and butyl hexanoate were calculated at 15.5, 11.4, and 4.8 mg/day, respectively. Longevity of this system was calculated to be 64, 87, and 208 days, respectively.

Release rates for the thermoset urethane (Flexane® 80P) and synthetic rubbers systems ranged from 0.055 to 0.2 mg/cm$^2$/day, depending on durometer/hardness that is a measure of polymer crosslinking. Best results were obtained at durometer/hardness levels above D30. Release rates for the Saranex system without the release control provided by the metalized polyethylene and diffusion control orifice were 187, 236, and 7 mg/day for propyl propanoate, methyl tiglate, and butyl hexanoate, respectively.

The relative relationship between the size of a diffusion regulating orifice and a wide range in volatile compounds is shown in FIG. 4. For lower to high pressure compounds, below 10 mmHg, the release profiles were relatively linear with pore size. At high vapor pressures, above 50 mmHg, release rates were not linear and showed a rapid depletion of the carrier reservoir. Secondary carrier design, as noted with the thermoplastic absorbents and thermoset polymers, restricted the amount of active compounds actually available for diffusion through the regulating orifice.

Thus, we have devised a number of options to contain highly volatile bioactives, and provide a means for immobilizing the neat liquid compounds, that provide a means to employ various carriers to hold and restrict the volatility of the actives. We have also devised a secondary package to further control release rates and thus the concentration of the actives in air related to cockroach attraction. Our goal was to optimize both the air concentration related to efficacy and the longevity of the package to deliver this dose for 30-60 days. Several of these formulations were evaluated.

Evaluation of sustained release formulations: Three cockroach attractants (methyl tiglate, butyl heptanoate, and propyl proprionate) were formulated in one or more polymer formulations (Urethane, Pellethane, Santoprene, and/or Polyethylene) as indicated in Table 4. A sweater box (1.5×2.0×0.5 ft) provided the test arena. The sides of the arena were coated with a blend of mineral oil and Vaseline petroleum jelly. The tops of two 8 oz paper ice cream cups were tapped to the arena floor with masking tape and, prior to the addition of the test cockroaches, inverted cups without holes were fixed to the tapped lids. Twenty-five laboratory reared late stage nymphs or adult male German roaches (*B. germanica*), starved for 72 hrs, were added to the arena and allowed to calm down (ca. 1 hour). The starting inverted ice cream cups were carefully removed and each ice cream cup top was then supplied with a water-tube (1.5 ml scintillation vial with water and stoppered with cotton), one lab chew food pellet, and either a test attractant polymer formulation or the corresponding polymer blank control. The ice cream cups were replaced with different cups that had a roach entrance hole (1.5 cm diameter) cut into it, just above the inverted cup top (near the arena floor). The cups were oriented so that the holes were facing each other. The number of roaches that sought harborage in the cups was counted after 24 hours by plugging the entrance holes with cotton, the roaches inside euthanized, and the numbers in each cup counted. The experimental observer did not know the composition of the samples evaluated.

Results: The experiment evaluated the response of male roaches to two potential harborages, one containing an attractant to be evaluated and the other a control harborage. The results for methyl tiglate (MeTi) formulated with several sustained release polymer formulations are shown in FIG. 5. Methyl tiglate formulated with Santoprene showed significant attraction and aggregation to the treatment harborage.

Results for propyl propanoate (ProProp) and butyl hexanoate (BuHe) in several polymer formulations are shown in FIG. 6. Propyl propanoate was only formulated in urethane; however, the results showed significant attraction and subsequent aggregation in the treatment harborage. Butyl hexanoate in Santoprene also gave significant attraction and subsequent aggregation in the treatment harborage. The other attractant polymer formulations did not yield significant attraction.

These results were obtained over a 6-month period of time using the same formulated materials, which demonstrated the stability of the polymer attractant formulation. Sustained release formulations were shown to be effective in attracting and holding German cockroaches in a harborage. If the attractant was formulated with a suitable insecticide, or if the insecticide was formulated with a food product, then the result would be control of the target roaches. Roach attractants can counteract behavioral avoidance of commercially available cockroach baits, which has been the reason for many costly control failures.

Competition in the cockroach control market is intense. Innovations are continually being sought to provide a competitive advantage. This is the first report of the identification of cockroach attractants. Successful incorporation of this invention into "roach motel" type products will provide distinct advantages over other products in the market; for example, increased speed and efficacy of action, action detection thresholds, and elimination by attracting cockroaches to a "killing zone". The attractants are effective at low concentrations, 0.5% (W/V) in mineral oil, and are commercially available at low cost, e.g. butyl hexanoate=$4.50/lb, propyl propanoate=$14.00/lb.

All of the references cited herein, including U.S. Patents, are incorporated by reference in their entirety.

Thus, in view of the above, the present invention concerns (in part) the following:

A method for attracting cockroaches to an object or area, comprising (or consisting essentially of or consisting of) treating said object or area with a composition comprising a cockroach attracting effective amount of at least one (or two or three or four or more than one) compound selected from the group consisting of methyl, ethyl, propyl, or butyl esters of $C_{3-7}$ saturated or unsaturated carboxylic acids and mixtures thereof, and optionally a carrier material or carrier.

The above method, wherein said composition contains ethyl propanoate, ethyl pentanoate, ethyl hexanoate, propyl propanoate, butyl hexanoate, butyl heptanoate, methyl tiglate, ethyl hexanoate, or mixtures thereof. The above method, wherein said composition contains ethyl propanoate. The above method, wherein said composition does not contain ethyl propanoate. The above method, wherein said composition contains ethyl pentanoate. The above method, wherein said composition does not contain ethyl pentanoate. The above method, wherein said composition contains ethyl hexanoate. The above method, wherein said composition does not contain ethyl hexanoate. The above method, wherein said composition contains propyl propanoate. The above method, wherein said composition does not contain propyl propanoate. The above method wherein said composition contains butyl hexanoate. The above method, wherein said composition does not contain butyl hexanoate. The above method, wherein said composition contains butyl heptanoate. The above method, wherein said composition does not contain butyl heptanoate. The above method, wherein said composition contains methyl tiglate. The above method, wherein said composition does not contains methyl tiglate. The above method, wherein said composition contains ethyl hexanoate. The above method, wherein said composition does not contain ethyl hexanoate.

The above method, wherein said cockroaches are selected from the group consisting of *Blattella germanica, Periplaneta americana, Blatta orientalis, Supella supellectilium*, and mixtures thereof. The above method, wherein said cockroaches are *Blattela germanica.*

The above method, wherein said cockroaches are male cockroaches.

The above method, wherein said carrier is a thermoplastic polymer.

The above method, wherein said carrier is a thermoplastic polymer comprised of 4-(1,1,3,3-tetramethylbutyl) and ethylene-5-ethylidenebicyclo[2.2.1]hept-2-ene-propene thermoplastic synthetic rubber.

The above method, wherein said carrier is a thermoplastic polymer comprised of a polyester polycaprolactone polyurethane.

The above method, wherein said carrier is a thermoplastic polymer comprised of polypropylene glycol, and methylene bis(4-cyclohexylisocyanate).

The above method according to claim 1, wherein said carrier is a octadecylammonium ion-substituted nanoclay.

A method for repelling cockroaches from an object or area, comprising (or consisting essentially of or consisting of) treating said object or area with a cockroach repelling composition comprising a cockroach repelling effective amount of at least one (or two or three or four or more than one) compound selected from the group consisting of methyl, ethyl, propyl, or butyl esters of $C_{3-7}$ saturated or unsaturated carboxylic acids and mixtures thereof, and optionally a carrier material or carrier.

The above method, wherein said composition contains propyl butanoate, butyl propanoate, butyl butanoate, hexyl butanoate, or mixtures thereof. The above method, wherein said composition contains propyl butanoate. The above method, wherein said composition does not contain propyl butanoate. The above method wherein said composition contains butyl propanoate. The above method, wherein said composition does not contain butyl propanoate. The above method, wherein said composition contains butyl butanoate. The above method, wherein said composition does not contain butyl butanoate. The above method, wherein said composition contains hexyl butanoate. The above method, wherein said composition does not contain hexyl butanoate.

The above method, wherein said cockroaches are selected from the group consisting of Blattella germanica, Periplaneta americana, Blatta orientalis, Supella supellectilium, and mixtures thereof. The above method, wherein said cockroaches are Blattela germanica.

The above method, wherein said cockroaches are male cockroaches.

The above method, wherein said carrier is a thermoplastic polymer.

The above method, wherein said carrier is a thermoplastic polymer comprised of 4-(1,1,3,3-tetramethylbutyl) and ethylene-5-ethylidenebicyclo[2.2.1]hept-2-ene-propene thermoplastic synthetic rubber.

The above method, wherein said carrier is a thermoplastic polymer comprised of a polyester polycaprolactone polyurethane.

The above method, wherein said carrier is a thermoplastic polymer comprised of polypropylene glycol and methylene bis(4-cyclohexylisocyanate).

The above method according to claim 1, wherein said carrier is a octadecylammonium ion-substituted nanoclay.

A composition (for attracting or repelling cockroaches) comprising (or consisting essentially of or consisting of) at least one compound (or two or three or four or more than one) selected from the group consisting of methyl, ethyl, propyl, or butyl esters of $C_{3-7}$ saturated or unsaturated carboxylic acids and mixtures thereof, and optionally a carrier or carrier material.

The above composition, wherein said composition contains a carrier or carrier material.

The above composition, wherein said composition comprises at least two compounds selected from the group consisting of methyl, ethyl, propyl, or butyl esters of $C_{3-7}$ saturated or unsaturated carboxylic acids and mixtures thereof, and optionally a carrier or carrier material.

The above composition, wherein said composition comprises at least three compounds selected from the group consisting of methyl, ethyl, propyl, or butyl esters of $C_{3-7}$ saturated or unsaturated carboxylic acids and mixtures thereof, and optionally a carrier or carrier material.

The above composition, wherein said composition comprises at least four compounds selected from the group consisting of methyl, ethyl, propyl, or butyl esters of $C_{3-7}$ saturated or unsaturated carboxylic acids and mixtures thereof, and optionally a carrier or carrier material.

Other embodiments of the invention will be apparent to those skilled in the art from a consideration of this specification or practice of the invention disclosed herein. It is intended that the specification and examples be considered as exemplary only with the true scope and spirit of the invention being indicated by the following claims.

TABLE 1

Olfactometer results (percent response to a 0.5% solution of the test compound in mineral oil) for various esters. Results with an * after them are significantly attractive; compounds with ** after them are significantly repellent (mean of 3 replicates).

| Test Compound | Percent Response |
| --- | --- |
| Methyl Propanoate | 60.0 |
| Methyl Butanoate | 55.0 |
| Methyl Pentanoate | 50.0 |
| Methyl Hexanoate | 45.0 |
| Methyl Heptanoate | 50.0 |
| Methyl Nonanoate | 45.0 |
| Methyl Decanoate | 55.0 |
| Methyl Undecanoate | 45.0 |
| Methyl Dodecanoate | 45.0 |
| Ethyl Propanoate | 65.0* |
| Ethyl Butyrate | 63.3 |
| Ethyl Pentanoate | 65.0* |
| Ethyl Hexanoate | 75.0* |
| Ethyl Heptanoate | 40.0 |
| Ethyl Octanoate | 50.0 |
| Propyl acetate | 40.0 |
| Propyl Propanoate | 70.0* |
| Propyl Butanoate | 35.0** |
| Butyl Acetate | 45.0 |
| Butyl Propanoate | 15.0** |
| Butyl Butanoate | 35.0** |
| Butyl Pentanoate | 50.0 |
| Butyl Hexanoate | 75.0* |
| Butyl Heptanoate | 80.0* |
| Butyl Octanoate | 55.0 |
| Butyl Nonanoate | 40.0 |
| Hexyl Butanoate | 35.0** |

TABLE 2

Olfactometer results for six controlled release formulations after aging in a fume hood for one hour (mean of 3 replicates).

| Test Compound | Absorbent | Percent Response |
| --- | --- | --- |
| methyl tiglate | Charcoal | 76.6 |
| butyl hexanoate | Charcoal | 82.0 |
| propyl propanoate | Charcoal | 65.0 |
| butyl heptanoate | Charcoal | 70.0 |
| Blank | Charcoal | 48.3 |
| methyl tiglate | Molecular Sieve | 50.0 |
| propyl propanoate | Molecular Sieve | 50.0 |

TABLE 3

Olfactometer results for three controlled release formulations after aging in a fume hood for three time periods (mean of 3 replicates).

| Test Compound | Time Aged (Hours) | Percent Response |
|---|---|---|
| methyl tiglate | 1 | 76.6 |
| methyl tiglate | 24 | 66.7 |
| methyl tiglate | 48 | 61.6 |
| butyl hexanoate | 1 | 82.0 |
| butyl hexanoate | 24 | 70.0 |
| butyl hexanoate | 48 | 61.6 |
| butyl heptanoate | 1 | 70.0 |
| butyl heptanoate | 24 | 61.6 |
| butyl heptanoate | 48 | 58.3 |

TABLE 4

Sustained release polymer formulated with the indicated roach attractant.

| POLYMER | ROACH ATTRACTANT |
|---|---|
| Urethane | methyl tiglate |
| Urethane | butyl hexanoate |
| Urethane | propyl propanoate |
| Pellethane | methyl tiglate |
| Santoprene | methyl tiglate |
| Polythylene | methyl tiglate |
| Pellethane | butyl heptanoate |
| Santoprene | butyl heptanoate |

We claim:

1. A method for attracting cockroaches to an object or area, comprising treating said object or area with a composition comprising a cockroach attracting effective amount of ethyl pentanoate, optionally at least one compound selected from the group consisting of ethyl hexanoate, butyl hexanoate, ethyl propanoate, propyl propanoate, butyl heptanoate, methyl tiglate, and mixtures thereof, and optionally a carrier material or carrier.

2. The method according to claim 1, wherein said cockroaches are selected from the group consisting of *Blattella germanica*, *Periplaneta americana*, *Blatta orientalis*, *Supella supellectilium*, and mixtures thereof.

3. The method according to claim 1, wherein said cockroaches are *Blattela germanica*.

4. The method according to claim 1, wherein said cockroaches are male cockroaches.

5. The method according to claim 1, wherein said carrier is a thermoplastic polymer.

6. The method according to claim 1, wherein said carrier is a thermoplastic polymer comprised of 4-(1,1;3,3-tetramethylbutyl) and ethylene-5-ethylidenebicyclo[2.2.1]hept-2-ene-propene thermoplastic synthetic rubber.

7. The method according to claim 1, wherein said carrier is a thermoplastic polymer comprised of a polyester polycaprolactone polyurethane.

8. The method according to claim 1, wherein said carrier is a thermoplastic polymer comprised of polypropylene glycol and methylene bis(4-cyclohexylisocyanate).

9. The method according to claim 1, wherein said carrier is a octadecylammonium ion-substituted nanoclay.

10. The method according to claim 1, said method consisting of treating said object or area with a composition comprising a cockroach attracting effective amount of ethyl pentanoate, optionally at least one compound selected from the group consisting of ethyl hexanoate, butyl hexanoate, ethyl propanoate, propyl propanoate, butyl heptanoate, methyl tiglate, and mixtures thereof, and optionally a carrier material or carrier.

11. The method according to claim 1, wherein said composition does not contain ethyl propanoate.

12. The method according to claim 1, wherein said composition does not contain propyl propanoate.

13. The method according to claim 1, wherein said composition does not contain methyl tiglate.

14. A method for attracting cockroaches to an object or area, comprising treating said object or area with a composition comprising a cockroach attracting effective amount of at least one compound selected from the group consisting of ethyl pentanoate, ethyl hexanoate, butyl hexanoate, butyl heptanoate, and mixtures thereof, and optionally a carrier material or carrier, wherein said cockroach attracting effective amount is 2.5 µg/µl to 8.5 µg/µl.

* * * * *